US00PP30052P3

(12) United States Plant Patent
Hansen

(10) Patent No.: US PP30,052 P3
(45) Date of Patent: Jan. 1, 2019

(54) ***PENSTEMON* PLANT NAMED 'BLACKBEARD'**

(50) Latin Name: *Penstemon digitalis*
Varietal Denomination: Blackbeard

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 55 days.

(21) Appl. No.: 15/530,316

(22) Filed: Dec. 21, 2016

(65) Prior Publication Data

US 2018/0177103 P1 Jun. 21, 2018

(51) Int. Cl.
*A01H 5/02* (2018.01)

(52) U.S. Cl.
USPC ..... Plt./465
CPC ..... *A01H 5/02* (2013.01)

(58) Field of Classification Search
USPC ..... Plt./465
CPC ... A01H 5/02; A01H 5/00; A01H 5/12; A01H 6/68
See application file for complete search history.

(56) References Cited

U.S. PATENT DOCUMENTS

PP24,804 P2 * 8/2014 Horvath ..... A01H 5/02 Plt./465

OTHER PUBLICATIONS

Walters Gardens, Inc. Summer 2016-Spring 2017 catalog, retrieved on Jan. 18, 2018, retrieved from the Internet at https://cld.bz/users/user-9rLuGlj/Walters-Gardens-2017-catalog/204, pp. 1, 6-9, 165, 202-203. (Year: 2017).*

* cited by examiner

*Primary Examiner* — June Hwu

(57) ABSTRACT

The new and distinct cultivar of ornamental, winter-hardy, beardtongue plant, *Penstemon* 'Blackbeard' with strictly upright, tightly-compact strong stems, lilac purple flowers for about four weeks and dark purple foliage. Useful in the landscape as a specimen plant, en masse or contain plant, and attractive to hummingbirds.

1 Drawing Sheet

Botanical classification: *Penstemon digitalis.*
Variety denomination: 'Blackbeard'.

BACKGROUND OF THE INVENTION

The present invention relates to a new and distinct plant of beardtongue, botanically known as *Penstemon* 'Blackbeard' and will be referred to hereinafter also by its cultivar name 'Blackbeard' and the new plant. The new plant cultivar of beardtongue is a hardy herbaceous perennial grown for landscape use.

*Penstemon* 'Blackbeard' is a seed selection derived from selfed *Penstemon* 'Pocahontas' U.S. Plant Pat. No. 24,804. Seeds were collected by the inventor and sown in the fall of 2013, germinated in a greenhouse in spring 2014 and planted in a research field that same year at a wholesale perennial nursery in Zeeland, Mich. All subsequent evaluations were performed in a full-sun trial garden at the same nursery with loamy sand soil and irrigation and fertilizer as required. The single seedling plant was selected for further evaluation during the summer of 2014. The new plant was propagated by basal shoot cuttings at the same nursery in Zeeland, Mich., and the original plant and the cuttings evaluated over the next two years until final approval for introduction in the summer of 2014. The resultant asexually propagated cuttings have been stable and identical to the original plant in successive asexual propagations.

No plants of *Penstemon* 'Blackboard' have been sold or disclosed in this country, or anywhere in the world, by this or any name, more than one year prior to the filing of this application, with the exception of that which was sold or disclosed either directly or indirectly from the inventor.

SUMMARY OF THE INVENTION

*Penstemon* 'Blackbeard' differs from its parent as well as all other hardy beardtongue known to the inventor in a combination of traits. The following characteristics in combination distinguish 'Blackbeard' from all other beardtongue plants known to the inventor:

1. Strictly upright growth with tightly-compact strong stems;
2. Foliage developing dark purple coloration in high light intensity;
3. Flowering with lilac purple horizontal flowers for four weeks beginning early summer in Michigan.

The nearest comparison plants are the parent plant *Penstemon* 'Pocahontas' U.S. Plant Pat. No. 24,804 and 'Dark Towers' U.S. Plant Pat. No. 20,013. Compared with 'Pocahontas' the new plant has flowers that are darker lilac purple, the foliage is darker and the habit is slightly shorter. Compared with 'Dark Towers' the new plant is more compact and shorter in habit, and the flowers are darker lilac purple.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color. The plant used in the photograph is a two-year-old plant grown in full sun field in loamy sand soil in trial gardens of a nursery in Zeeland, Mich.

DETAILED BOTANICAL DESCRIPTION

Figure 1:
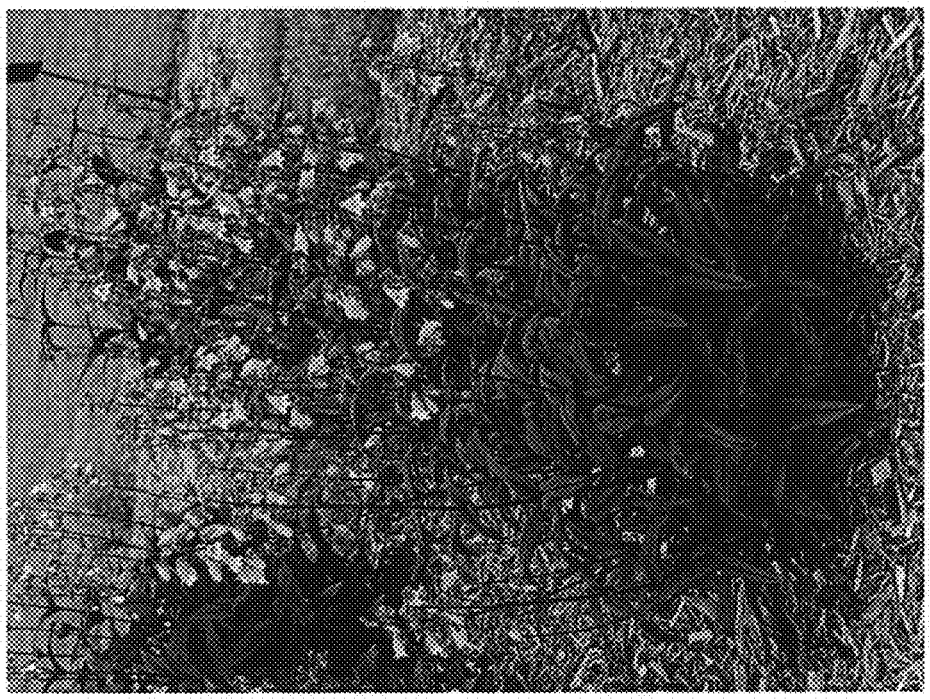
FIG. 1 shows 'Blackbeard' in the landscape.
Figure 2:
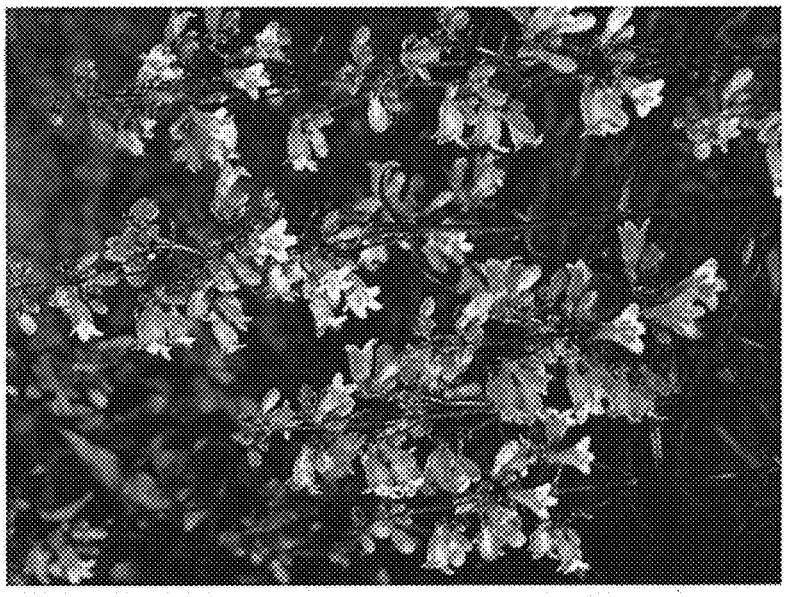
FIG. 2 shows a close-up of the flower stems of 'Blackbeard'.

The following is a detailed description of *Penstemon* 'Blackbeard' as observed and compared to other cultivars for two years in trial gardens and production fields at a nursery in Zeeland, Mich. The following description is of a two-year-old plant of *Penstemon* 'Blackboard' in a full-sun display garden in Zeeland, Mich. with limited supplemental fertilizer and irrigation as needed and without any pinching or plant growth regulators. The new plant has not been observed under all possible environments, and the phenotype may vary slightly with different environmental conditions, such as temperature, light, fertility, moisture and maturity levels, but without any change in the genotype. The color descriptions are in accordance with the 2001 edition of The R.H.S. Colour Chart of The Royal Horticultural Society, London, England, except where common dictionary color terms are used.

Plant habit: Herbaceous winter-hardy, perennial with upright overall form; with new stems emerging from the base each spring; about 30 to 40 stems per plant; flowering in branched panicle;

Plant size: About 86.0 cm in height, average stem 80.0 cm tall, and about 77.5 cm in width about 60 cm above soil;

Root description: Fibrous, well-branched, developing to thickness of about 1.0 mm; color between RHS 161A and RHS 161B;

Propagation: Shoot-tip cuttings; root initiation occurs in about 14 days at a temperature of 22° C.;

Growth rate: Moderately vigorous;

Crop time: About 12 to 14 weeks to finish in a 4 liter pot from rooted plug;

Stem description: Terete; oppositely branched in distal region; glabrous; lustrous; average about 80.0 cm long and about 7.0 mm across near base;

Stem color: Nearest RHS 187B;

Internode: Average about 10 per stem, average internode length about 5.7 cm, larger toward flowers;

Internode color: Same as surrounding stem;

Foliage description: Simple; typically opposite; basal leaves oblanceolate, acute apex and sessile, attenuate, clasping base; cauline leaves lanceolate, narrowly acute apex and sessile, rounded clasping base; margin entire, nearly microscopically ciliolate; abaxial and adaxial surface glabrous, slightly lustrous adaxial and matte abaxial; fragrance not detected;

Leaf size: Basal leaves to about 22.0 cm long and about 6.5 mm wide; cauline leaves about 8.5 cm long and about 2.2 cm wide;

Leaf color: Lower basal leaves blend between RHS 137A and RHS 139A with blush of nearest RHS 187A, abaxial leaves nearest RHS 137A with blush of between RHS 187A and RHS 187B; cauline adaxial nearest RHS 184C; cauline abaxial nearest RHS 187B;

Leaf venation: Pinnate;

Vein color: Adaxial midrib between RHS N186C and RHS N186D, secondary veins nearest RHS N186D; abaxial midrib between RHS 182B and RHS 182A, and secondary veins nearest RHS N186D;

Petiole: Leaves sessile;

Peduncle: Branched panicle; smooth, glabrous; main stems vertical, branched at about 20 degrees below vertical; flowering portion to about 17.7 cm long and about 6.6 cm across; up to 70 flowers per panicle;

Peduncle color: Nearest RHS 187B;

Branches: Terete; opposite; glabrous, lustrous; lower branches about 5.0 cm long and about 2.0 mm diameter, decreasing distally;

Branch color: Nearest RHS 187B;

Pedicel: Terete; pubescent; average about 4.5 cm long and less than 1.0 mm diameter;

Pedicel color: Nearest RHS 187B;

Flower buds about one day prior to opening: About 22.0 mm long and about 6.0 mm wide; oblong ovoid; rounded apex; basal about 8.0 mm narrowed to a tube about 3.5 mm diameter, with rounded base;

Bud color: Unopened petal portion nearest RHS 75A;

Flowers: Zygomorphic; perfect; bilabiate with upper and lower lip fused in about basal 16.5 mm; about 27.0 mm long and about 20.0 mm across; face opening to nearly flat; lasting about five to seven days;

Flower attitude: Mostly outward;

Fragrance: None detected;

Corolla: Glandular abaxial, glabrous adaxial; bilabitate, fused in basal 22.0 mm, with upper lip consisting of two lobes each about 4.5 mm across and 5.0 mm long; lower lip consisting of three lobes with center lobe about 5.0 mm across and 5.0 mm long and two side lobes about 6.0 mm across and 5.0 mm long; lobes with rounded apex and entire margin; average length about 27.0 mm long, about 20.0 mm across at face, about 10.0 cm diameter in central tube and about 4.0 mm diameter in basal one-third of tube;

Corolla color: Abaxial between RHS N80D and RHS 75A; adaxial lobe face between RHS 75A and RHS N80D; adaxial tube center nearest RHS N155C; abaxial corolla between RHS N80D and RHS 75A;

Gynoecium: One pistil;

*Style*.—About 23.0 mm long and less than about 2.0 mm wide; color white, lighter than RHS 155D.

*Stigma*.—Oblong, about 0.5 mm wide and about 0.7 mm long; color nearest RHS 155D.

Androecium: Four;

*Filaments*.—About 20.0 mm long and about 1.0 mm in diameter; color nearest RHS 155D.

*Anther*.—Elliptic; about 1.0 mm long and 0.5 mm across, versatile; color nearest RHS N186A.

*Pollen*.—Abundant color nearest RHS 155D.

Calyx: Stellate, campanulate, fused at base; not adpressed to corolla; about 5.0 mm long and about 10.0 mm across;

Sepals: Five; lanceolate, narrowly acute apex and fused base, entire margin; to about 1.5 mm wide above fusion point and 5.0 mm long; glabrous abaxial and adaxial;

Sepal color: Abaxial color abaxial and adaxial color both nearest RHS N186B;

Fruit: Septicidal capsule; ovoid with acute apex and rounded base; about 10.0 mm long and 5.5 mm across; color as developing nearest RHS N186C and with maturity between RHS 165A and RHS 165B;

Seed: Irregular; about 1.0 mm long and about 1.0 mm diameter; color between RHS 200A and RHS 202A;

*Hardiness to at least U.S.D.A. zones* 3 *to* 8.—The new plant perform best with good drainage and is resistant to drought once established.

*Pest and disease resistance*.—Not known to show resistance beyond that typical of beardtongue plants. No other susceptibility or resistance to diseases or pests has been observed except that which is common to *Penstemon.*

It is claimed:

1. A new and distinct cultivar of hardy beardtongue plant, *Penstemon* 'Blackbeard' as herein described and illustrated.

* * * * *